US006171571B1

(12) United States Patent
Bedard et al.

(10) Patent No.: US 6,171,571 B1
(45) Date of Patent: Jan. 9, 2001

(54) CRYSTALLINE MULTINARY METAL OXIDE COMPOSITIONS, PROCESS FOR PREPARING AND PROCESSES FOR USING THE COMPOSITION

(75) Inventors: Robert L. Bedard, McHenry; Paula L. Bogdan, Mt. Prospect; Lisa M. King, Crystal Lake; Susan C. Koster, South Elgin, all of IL (US)

(73) Assignee: UOP LLC, Des Plaines, IL (US)

( * ) Notice: Under 35 U.S.C. 154(b), the term of this patent shall be extended for 0 days.

(21) Appl. No.: 09/309,040

(22) Filed: May 10, 1999

(51) Int. Cl.[7] .......................... C07C 253/26; B01J 23/20; B01J 23/24; C01G 33/00; C01G 39/00

(52) U.S. Cl. .................. 423/593; 423/508; 423/606; 423/641; 502/215; 502/311; 502/312; 502/317; 502/353; 558/321; 558/322; 558/323; 558/325

(58) Field of Search ..................................... 423/508, 593, 423/606, 641; 501/134; 502/215, 311, 312, 317, 353; 558/321, 322, 323, 325

(56) References Cited

U.S. PATENT DOCUMENTS

| 3,371,125 | * | 2/1968 | McMahon | 502/311 |
|---|---|---|---|---|
| 4,234,461 | * | 11/1980 | Suresh et al. | 502/311 |
| 4,250,346 | | 2/1981 | Young et al. | 585/658 |
| 4,339,355 | | 7/1982 | Decker et al. | 252/464 |
| 4,524,236 | * | 6/1985 | McCain | 501/312 |
| 4,596,787 | | 6/1986 | Manyik et al. | 502/312 |
| 4,892,856 | | 1/1990 | Kawajiri et al. | 502/247 |
| 5,206,201 | * | 4/1993 | Kishimoto et al. | 502/312 |
| 5,512,305 | * | 4/1996 | Abrams et al. | 423/593 |
| 5,750,760 | | 5/1998 | Ushikubo et al. | 558/319 |
| 5,807,531 | | 9/1998 | Hibst et al. | 423/593 |
| 6,063,728 | * | 5/2000 | Hinago et al. | 502/311 |

FOREIGN PATENT DOCUMENTS 5-208136 * 8/1993 (JP) ........................... 502/312

OTHER PUBLICATIONS

H. Werner et al., *Catalysis Letters*, 44, (1997) pp. 153–63, Relevance of a glassy nanocrystalline state of $Mo_4VO_{14}$ for its action as selective oxidation catalyst.

E.M. Thornsteinson, et al., *Journal of Catalysis*, 52, pp. 116–132, (1978), "The Oxidative Dehydrogenation of Ethane over Catalysis Containing Mixed Oxides of Molybdenum and Vanadium".

Burch et al., *Applied Catalysis*, 70. 129–148 (1992).
Burch et al., *Topics in Catalysis*, 3, 355–364 (1996).
Ueda et al. *Chem. Commun.*, 517–518, 1999.

\* cited by examiner

Primary Examiner—Mark L. Bell
Assistant Examiner—David Sample
(74) Attorney, Agent, or Firm—John G. Tolomei; Frank S. Molinaro

(57) ABSTRACT

A new family of crystalline metal oxide compositions have been synthesized. These compositions are described by the empirical formula:

$$A_n Nb M_x M'_y M''_m O_p$$

where A is an alkali metal cation, ammonium ion and mixtures thereof, M is tungsten, molybdenum, or mixtures thereof. M' is vanadium, tantalum and mixtures thereof, and M" is antimony, tellurium and mixtures thereof. M' and M" are optional metals. These compositions are characterized by having an x-ray diffraction pattern having at least one peak at a d spacing of about 3.9 Å. A hydrothermal synthesis procedure as well as processes using the composition, e.g., ammoxidation of propane, are also disclosed.

24 Claims, No Drawings

CRYSTALLINE MULTINARY METAL OXIDE COMPOSITIONS, PROCESS FOR PREPARING AND PROCESSES FOR USING THE COMPOSITION

FIELD OF THE INVENTION

This invention relates to a new family of crystalline metal oxide compositions. These compositions contain niobium, an alkali metal, at least one M metal where M is tungsten or molybdenum, optionally a M' metal such as vanadium and a M" metal such as antimony. This invention also relates to a hydrothermal process for preparing the crystalline compositions and to an ammoxidation process using the compositions.

BACKGROUND OF THE INVENTION

Olefins, e.g., propylene or isobutene are used to prepare a number of higher value products such as aldehydes, acids and nitriles. Since the price of the corresponding alkanes, i.e., propane or isobutane is lower than that of the olefins, it would be advantageous to be able to produce the higher value product directly from the alkanes.

Attempts have been made to synthesize novel materials to catalyze the selective oxidation of paraffins. One such catalyst is described in U.S. Pat. No. 5,750,760 where it is disclosed that a multinary composition having the empirical formula:

$$Mo_aV_bSb_cX_xO_n$$

where X is an element such as Nb, Ta, W etc. can catalyze the oxidation of an alkane with ammonia in the presence of oxygen. Other compositions which have been disclosed in the art include a $Mo_4VO_{14}$ phase by H. Werner et al. in *Catalysis Letters*, 44 (1997) 153–63. In *J. Catalysis* 52, 116–132 (1978), E. M. Thorsteinson et al., describe a mixed oxide catalyst containing molybdenum and vanadium along with another transition metal such as Ti, Nb, Ta, etc. The authors present activity data and physically characterize the compositions. MoVNb systems have also been described in *Applied Catalysis*, 70 129–148 (1991) and *Topics in Catalysis* 3, 355–364 (1996). U.S. Pat. No. 4,524,236 discloses a composition containing molybdenum, vanadium, niobium, antimony plus at least one metal such as lithium, barium, titanium etc. U.S. Pat. No. 4,339,355 discloses a composition comprising $Mo_aV_bNb_cX_d$, where X is Co, Cr, Cu, Fe, In, Mn and/or Y. It is further disclosed that the compositions have spinel or perovskite structures. In U.S. Pat. No. 4,596,787 a catalyst comprising $Mo_aV_bNb_cSb_dX_e$ is disclosed, where X includes Li, Sc, Na, Fr, Ta, etc. U.S. Pat. No. 4,250,346 discloses a catalyst with an empirical formula of $Mo_aX_bY_c$, where X is Cr, Mn, Nb, Ta, Ti, V and/or W and Y=Bi, Ce, Co, Cu, Fe, K, Mg, Ni, P, Pb, Sb, Si, Sn, Ti and/or U. U.S. Pat. No. 4,892,856 discloses a catalyst having the composition $Mo_aV_bA_cB_dC_eD_fO_x$ where A is tungsten or niobium, B is Fe, Cu, Bi, Cr, Sb or Tl, C is an alkali or alkaline earth metal and D is Si, Al or Ti. U.S. Pat. No. 5,807,531 discloses a multimetaloxide having an empirical formula of $Mo_{12-a-b-c}V_aM^1{}_bM^2{}_cO_x$. However, these materials have a low surface area of 17 m²/g or lower. Finally, Ueda et al., in *Chem. Commun.*, 1999, 517–518, disclose a Mo—V—M—O(M=Al, Fe, Cr and Ti) composition which is hydrothermally synthesized. Although these compositions have a diffraction peak at about 3.9 Å, they do not have applicant's empirical formula (see below).

In contrast to these reports, applicants have synthesized a new family of crystalline oxide compositions based on niobium, at least one of tungsten and molybdenum, and optionally another metal such as vanadium, tantalum, antimony or tellurium. These novel compositions are prepared hydrothermally and are characterized in that they have an x-ray diffraction pattern with at least one peak at a d spacing of about 3.9 Å and a high surface area. These materials show good activity for converting propane to acrylonitrile.

SUMMARY OF THE INVENTION

As stated, this invention relates to a new family of crystalline compositions, a process for preparing these compositions and a process which uses the compositions. Accordingly, one embodiment of the invention is a crystalline metal oxide composition having an empirical formula of:

$$A_nNbM_xM'_yM''_mO_p$$

where A is an alkali metal ion, ammonium ion or mixtures thereof, M is selected from the group consisting of molybdenum, tungsten or mixtures thereof, M' is tantalum and M" is selected from the group consisting of antimony, tellurium and mixtures thereof, "n" varies from about 0.1 to about 2, "x" varies from about 0.01 to about 4, "y" varies from zero to about 4, "m" varies from about zero to about 0.9 and "p" has a value such that it balances the valence of the combined elements A, Nb, M, M', M", the composition characterized in that it has at least one x-ray diffraction peak at a d spacing of about 3.9±0.15 Å. M' can also be vanadium and mixtures of vanadium and tantalum. When M is molybdenum or a mixture of tungsten and molybdenum, M' is vanadium and y>0, then the composition has a surface area of at least 25 m²/g.

Another embodiment of the invention is a process for preparing the crystalline compositions described above. The process comprises forming a reaction mixture containing reactive sources of A, niobium, M, optionally M' and optionally M" at a temperature and a time sufficient to form the crystalline composition, the mixture having a composition expressed in terms of mole ratios of oxides of:

$$aA_2O:NbO_{5/2}:bMO_3:cM'O_{5/2}:dM''O_{q/2}:eH_2O$$

where "a" has a value from about 0.75 to about 4, "b" has a value of about 0.02 to about 5, "c" has a value from 0 to about 5, "d" has a value from 0 to about 1, "q" is the valence of M" and "e" has a value of about 10 to about 500.

Yet another embodiment of the invention is a process for the ammoxidation of alkanes comprising reacting an alkane with ammonia in the presence of oxygen over an ammoxidation catalyst at ammoxidation conditions to produce a nitrile. The ammoxidation catalyst comprises one of the compositions described above, while the alkane is propane, isobutane or mixtures thereof.

These and other embodiments will become clearer after a detailed description of the invention.

DETAILED DESCRIPTION OF THE INVENTION

A new family of crystalline metal oxide compositions has been synthesized and characterized. These compositions contain niobium, at least one of tungsten and molybdenum, a third metal selected from vanadium or tantalum and a fourth metal selected from antimony and tellurium. A cation such as lithium is also present. These crystalline metal oxides are described by the empirical formula:

$$A_nNbM_xM'_yM''_mO_p$$

where "n" varies from about 0.1 to about 2. The value of "x" varies from about 0.01 to about 4, while the value of "y" varies from zero to about 4 and the value of "m" varies from zero to about 0.9. M is molybdenum, tungsten, or mixtures thereof, M' is selected from the group consisting of vanadium, tantalum and mixtures thereof, while M" is antimony, tellurium or mixtures thereof. Finally, A is an alkali metal cation, an ammonium cation or mixtures thereof. Examples of the alkali metals which can be used include: lithium, sodium, potassium, rubidium, cesium and mixtures thereof.

These novel crystalline metal oxide compositions are hydrothermally prepared. That is, a reaction mixture is prepared from reactive sources of the desired components along with water and heated at a temperature and for a time sufficient to form the desired product. Reactive sources of the alkali metals include the hydroxide, carbonate, halide, acetate, and sulfate compounds. Niobium reactive sources include niobium pentoxide ($Nb_2O_5$), hydrous niobium oxide, niobium ethoxide, and ammonium niobium oxalate. Molybdenum sources include molybdic acid (($NH_4$)$_6Mo_7O_{24}$·$4H_2O$), molybdenum trioxide ($MoO_3$), sodium molybdate and molybdenum (VI) oxychloride. Tungsten sources include ammonium tungstate, tungsten (VI) oxide, tungsten (VI) chloride, sodium tungstate, and tungstic acid. Vanadium sources include vanadium (V) oxide, vanadium (V) oxychloride, vanadium oxide sulfate, and ammonium vanadate. Tantalum sources include tantalum oxide, tantalum butoxide, tantalum bromide, and tantalum chloride. Tellurium sources include ammonium tellurium oxide, telluric acid, and tellurium oxide. It should be pointed out that this list is only by way of examples and other reactive sources of individual elements may also be used.

Using the above described reactive sources, a reaction mixture is formed which in terms of molar ratios of the oxides is expressed by the formula:

$$aA_2O:NbO_{5/2}:bMO_3:cM'O_{5/2}:dM"O_{q/2}:eH_2O$$

where "a" has a value from about 0.75 to about 4, "b" has a value of about 0.02 to about 5, "c" has a value from about 0 to about 5, "d" has a value from about 0 to about 1, "q" is the valence of M, "e" has a value of about 10 to about 500. Once the reaction mixture is formed, it is required that it have a pH of about 4 to about 10 and preferably from about 6 to about 9. This can be done by using a basic compound of the A cation. Alternatively, the A cation can be added as a non-basic compound and the pH adjusted by the addition of an appropriate amount of an organic base such as an alkyl amine or a tetraalkylammonium hydroxide.

Once the reaction mixture is formed and pH adjusted, it is reacted at a temperature of about 100–225° C. for a period of time of about 1 hr to about 96 hr in a sealed reaction vessel under autogenous pressure. After the allotted time, the mixture is filtered to isolate the solid product which is washed with deionized water and dried in air. Alternatively, the product may be isolated and washed by centrifugation techniques. The product may also be washed with aqueous acid rather than deionized water to convert the composition to the proton exchanged form during workup.

The crystalline metal oxide compositions of the invention are characterized by their unique x-ray diffraction pattern and their surface area. The x-ray diffraction pattern has at least one peak at a d spacing of about 3.9±0.15 Å. A second peak at ½ of the 3.9±0.15 Å spacing is also present in these compositions. Another X-ray diffraction peak, which is sometimes distinct but usually broad, is located at 10.7±0.25 Å. This peak is always broader than the 3.9 Å peak. Diffuse diffraction peaks are also located between 3.42 and 2.98 Å.

The crystalline metal oxide compositions of the invention are also characterized by their surface areas. These materials generally have a surface area of at least 15 $m^2/g$, and preferably at least 25 $m^2/g$. When the M metal is either molybdenum or a combination of molybdenum and tungsten, the M' metal is vanadium and y>0, then the surface area must be at least 25 $m^2/g$. These high surface areas are a result of the instant hydrothermal process.

The above described compositions can be ion exchanged so that the A cation is exchanged for another cation. These cations which can be exchanged into the metal oxide composition (secondary cations) include, without limitation, other alkali metal ions, hydronium ions, alkaline earth ions, lanthanide ions, divalent transition metal ions, trivalent transition metal ions and organic cations such as amphiphilic ammonium ions, quaternary ammonium cations and alkylpyridinium cations. Ion exchange can be carried out by means well known in the art. The process usually involves contacting the composition with a solution containing the desired cation at exchange conditions. Exchange conditions include a temperature of room temperature to about 100° C. and a time of about 20 minutes to 4 days.

The crystalline compositions of this invention can be used in various processes in which hydrocarbons are one of the reactants. An example of these processes is the ammoxidation of alkanes, such as propane and isobutane to provide nitrites, i.e., acrylonitrile and methacrylonitrile.

Conditions for ammoxidation may be found in the art and specifically in U.S. Pat. Nos. 4,788,173; 5,171,876 and 5,049,692 all of which are incorporated by reference. General conditions include a temperature of about 350° C. to about 700° C., an HSV of about 100 to about 10,000 $hr^{-1}$, an ammonia to alkane mole ratio of about 0.5:1 to about 3:1, an oxygen to ammonia mole ratio of about 0.5:1 to about 10:1 and a pressure of atmospheric to about 1034 kPa (150 psi). The sources of oxygen can be air, pure oxygen or oxygen with a diluent such as nitrogen, etc.

The following examples are set forth in order to more fully illustrate the invention. It is to be understood that the examples are only by way of illustration and are not intended as an undue limitation on the broad scope of the invention as set forth in the appended claims.

EXAMPLE 1

In a mortar there were mixed 1.64 g of $Li_2CO_3$ and 6.35 g of $MoO_3$ and ground to give a light green powder. To this there were added 6.86 g of $Nb_2O_5$·$12.2H_2O$ and the combined solids were then ground and added to a beaker containing 14.9 g of water. The resulting mixture was mixed, transferred to a PTFE-lined stainless steel reactor and heated under autogenous pressure in an oven at 150° C. for 24 hours. This mixture was designated as mixture A. Similar mixtures were prepared and reacted at various times and temperatures as follows: mixture B at 200° C. for 24 hours; mixture C at 150° C. for 48 hours; mixture D at 200° C. for 48 hours. After reaction, each product was isolated by centrifugation, washed with water and dried at room temperature.

All four products had substantially similar x-ray diffraction patterns with the main peak at about 3.9 Å. Analyses of products B and D gave respective anhydrous empirical formulas of: $Li_{0.26}NbMo_{0.61}O_p$ and $Li_{0.33}NbMo_{0.47}O_p$. The value of p was not determined in the analysis.

EXAMPLE 2

In a container there were mixed 1.03 g of product B from example 1 and a solution of 2M nitric acid and the mixture was stirred for 2 days at room temperature. The solid was isolated by filtration, washed with deionized water and dried in a dessicator equipped with calcium sulfate dessicant. Elemental analysis indicated an empirical formula of $NbMo_{0.55}O_p \cdot 0.67H_2O$. The powder X-ray diffraction pattern displayed higher intensity peaks but the pattern was otherwise unchanged from Product B of Example 1.

EXAMPLE 3

A slurry was prepared by mixing in a container 21.8 g of $Nb_2O_5 \cdot 12.2H_2O$ and 91.9 g of water followed by the addition of 16.41 g of $NH_4VO_3$, 49.51 g of $(NH_4)_6Mo_7O_{24} \cdot 4H_2O$ and 4.39 g of $NH_4OH$. The resulting yellow suspension was stirred for 1 hour, divided into aliquots which were placed into PTFE lined steel reactors and reacted as follows: 2A—150° C. for 24 hours, 2B—150° C. for 48 hours, 2C—200° C. for 48 hours; 2E —225° for 24 hours and 2F—225° C. for 48 hours. The reactor products were isolated by centrifugation and washed with 200 ml of $1M\ HNO_3$. Elemental analysis of sample 2A gave an empirical formula, expressed as anhydrous oxide, of $NbV_{0.23}Mo_{0.8}O_p$. The x-ray diffraction pattern of sample 2B and sample 2C were essentially identical to those of example 1, while the other samples showed the presence of impurities.

EXAMPLE 4

A series of compositions were prepared as described above and a description of the reaction mixture, synthesis conditions and empirical formulas are presented in Table 1. In each case, the major product was one displaying an x-ray powder diffraction pattern with peaks at about 3.91 Å, 1.96 Å and a peak at about 10.8 Å with varying degrees of broadness and definition.

TABLE 1

SUMMARY OF PREPARATION OF VARIOUS COMPOSITIONS

| Sample I.D. | Empirical Formula of Product (p not determined in analysis) | Reaction Mixture | Conditions | BET $m^2/g$ |
|---|---|---|---|---|
| 4A | $Li_{0.5}NbV_{0.23}Mo_{1.22}O_p$ | Li2O-0.32Nb2O5-0.5V2O5-2MoO3-45H2O | 24 hrs 150C | |
| 4B | $Li_{0.55}NbV_{024}Mo_{1.52}O_p$ | Li2O-0.32Nb2O5-0.5V2O5-2MoO3-45H2O | 24 hrs 200C | 32 |
| 4C | $Li_{0.52}NbV_{0.3}Mo_{1.39}O_p$ | Li2O-0.32Nb2O5-0.5V2O5-2MoO3-45H2O | 48 hrs 150C | 56 |
| 4D | $Li_{0.45}NbV_{0.21}Mo_{1.3}O_p$ | Li2O-0.32Nb2O5-0.5V2O5-2MoO3-45H2O | 48 hrs 200C | |
| 4E | $Li_{0.44}NbV_{0.15}Mo_{1.03}O_p$ | Li2O-0.48Nb2O5-0.25V2O5-2MoO3-47.5H2O | 48 hrs 150C | 166 |
| 4F | $Li_{0.34}NbV_{0.12}Mo_{0.8}O_p$ | Li2O-0.48Nb2O5-0.25V2O5-2MoO3-47.5H2O | 48 hrs 200C | 132 |
| 4G | $Na_{0.38}NbMo_{0.6}O_p$ | Na2O-1.64Nb2O5-2MoO3-50H20.O | 24 hrs 150C | |
| 4H | $Na_{0.31}NbMo_{0.5}O_p$ | Na2O-0.64Nb2O5-2MoO3-5OH2O | 24 hrs 200C | 105 |
| 4I | $Li_{0.5}NbV_{0.3}Mo_{1.49}O_p$ | Li2O-0.32Nb2O5-0.75V2O5-2MoO3-45H2O | 24 hrs 150C | 95 |
| 4J | $Li_{0.96}NbV_{1.38}Mo_{1.93}O_p$ | Li2O-0.32Nb2O5-0.75V2O5-2MoO3-45H2O | 24 hrs 200C | 41 |
| 4K | $Li_{1.27}NbV_{1.91}Mo_{2.1}O_p$ | Li2O-0.32Nb2O5-0.75V2O5-2MoO3-45H2O | 24 hrs 225C | 48 |
| 4L | $Li_{0.58}NbV_{0.3}Mo_{1.66}O_p$ | Li2O-0.32Nb2O5-0.75V2O5-2MoO3-45H2O | 48 hrs 150C | 86 |
| 4M | $Li_{1.26}NbV_{1.87}Mo_{2.26}O_p$ | Li2O-0.32Nb2O5-0.75V2O5-2MoO3-45H2O | 48 hrs 200C | 41 |
| 4N | $Li_{1.78}NbV_{2.13}Mo_{2.64}O_p$ | Li2O-0.32Nb2O5-0.75V2O5-2MoO3-45H2O | 48 hrs 225C | 29 |
| 4O | $Li_{0.53}NbV_{026}Sb_{0.35}Mo_{1.34}O_p$ | Li2O-0.26Nb2O5-0.5V2O5-0.10CSb2O5-2MoO3-44H2O | 24 hrs 225C | 78 |
| 4P | $Li_{0.63}NbV_{0.19}Sb_{0.2}Mo_{1.32}O_p$ | Li2O-0.32Nb2O5-0.25Sb2O5-0.25V2O5-2MoO3-45H2O | 24 hrs @ 150C | |
| 4Q | $NbMo_{1.1}V_{0.2}Sb_{1.05}O_p$ | Li2O-0.32Nb2O5-0.5V2O5-0.25Sb2O4-2MoO3-45H2O | 72 hrs. @ 150C* | 150 |
| 4R | $NbMo_{1.3}V_{0.48}Sb_{0.66}O_p$ | Li2O-0.32Nb2O5-1.5V2O5-1.25Sb2O4-2MoO3-45H2O | 72 hrs. @ 200C* | 113 |

*washed with aqueous $HNO_3$

EXAMPLE 5

Several of the compositions described in examples 1–4 were tested in a continuous flow fixed bed laboratory plant. The reactor consisted of a ¾" ID stainless steel tube reactor which contained a 10 cc catalyst bed volume. The propane, ammonia, air and nitrogen (diluent) were mixed at the top of the reactor and down flowed over the catalyst. The amount of catalyst in the bed can be varied from 2 cc to 10 cc with the remainder of the volume being taken up with inert quartz sand. The catalyst tests were carried out at the temperatures indicated in Table 2, and the effluent was analyzed by GC. Results of these tests are presented in Table 2.

TABLE 2

LABORATORY ACTIVITY RESULTS FOR SELECTED CATALYSTS

| Catalyst I.D. | Cat. Vol. (cc) | $C_3/NH_3/O_2$ | Flow Rate (cc/min) | Vol % $C_3$ | Test Temp. ° C. | $C_3$ Conv. (%) | ACN Selectivity (%) |
|---|---|---|---|---|---|---|---|
| 4Q | 2.5 | 1/1.2/1.6 | 117 | 7.5 | 440 | 24 | 25 |
| 4R | 2.0 | 1/1.2/1.6 | 117 | 7.5 | 417 | 19 | 18 |

The results in Table 2 show that the compositions of this invention can convert propane and selectively make acrylonitrile (ACN).

EXAMPLE 6

Into a mortar there were placed 1.64 g of $Li_2CO_3$ and 5.18 g, $WO_3$ which were ground together. To this there were added 3.56 g $Nb_2O_5 \cdot 12.2H_2O$ and the mixture ground well to give a damp yellow-green powder. This powder was added to a beaker containing 15.33 g of water, stirred for 1 hour, placed in a PTFE lined stainless steel reactor and heated under autogenous pressure in an oven for 168 hours at 150° C.

The solid product from this reaction was isolated by centrifugation, washed 3 times with about 200 ml of deionized water and dried at 100° C. Elemental analysis revealed the presence of 1.12% Li, 30.1% Nb, 42.9% W with an LOI of 5.87 mass %, giving a product formula of $Li_{0.50}NbW_{0.73}O_p \cdot 0.19H_2O$. X-ray powder diffraction revealed peaks at 3.91 and 1.96 Å, and a poorly defined broad peak at about 10.8 Å.

EXAMPLE 7

In a mortar, 1.80 g $Li_2CO_3$ was ground, followed by the addition of 10.25 g $WO_3$ and further grinding. Next, 6.90 g $Nb_2O_5 \cdot 12.2H_2O$ was added and the mixture was ground to yield a damp yellow-green powder. This powder was then added to a vessel containing 15.2 g of water and stirred for 1 hour after which the pH was 8.31. The resultant mixture was loaded into a PTFE lined stainless steel reactor and reacted for 48 hours at 200° C. After the reaction was completed, the solid reaction products were isolated by high-speed centrifugation. After centrifugation, the supernatant solution appeared to be colloidal and was decanted and retained as fines. The solids isolated by initial centrifugation were washed three times with 150 ml of deionized water and isolated by centrifugation. Each wash yielded colloidal supernatants that were decanted into the fines sample. The centrifuged supernatant containing the fines was then evaporated to dryness in a 100° C. forced air oven. X-ray powder diffraction patterns were characterized by the following data:

TABLE 3

| XRD Powder Diffraction Data for Course (fines) Products | | |
|---|---|---|
| 2-theta<br>Course (fines) | d (Å)<br>Course (fines) | I<br>Course (fines) |
| ~8, (8.5) | ~11, (10.39) | Poorly defined (Medium, broad) |
| 22.72 (22.72) | 3.91, (3.91) | Strong, (strong) |
| 46.42 (46.32) | 1.95, (1.95) | Weak (weak) |

Elemental analysis of the course and fines products revealed the following, in wt. %:

Course product: 1.20% Li, 22.9% Nb, 52.9% W with an LOI of 9.89 mass %, giving the empirical formula $Li_{0.7}NbW_{1.17}O_p$.

Fines product: 1.99% Li, 25.6% Nb, 46.1% W with an LOI of 9.97 mass %, giving the empirical formula $Li_{1.04}NbW_{0.92}O_p$.

We claim as our invention:

1. A crystalline metal oxide composition having an empirical formula of:

$$A_nNbM_xM'_yM''_mO_p$$

where A is a cation selected from the group consisting of an alkali metal ion, ammonium ion or mixtures thereof, M is molybdenum, tungsten and mixtures thereof, M' is selected from the group consisting of vanadium, tantalum and mixtures thereof, and M" is selected from the group consisting of antimony, tellurium and mixtures thereof, "n" varies from about 0.1 to about 2, "x" varies from about 0.01 to about 4, "y" varies from zero to 4, "m" varies from zero to about 0.9 and "p" has a value such that it balances the valence of the combined elements, A, Nb, M, M', M", the composition characterized in that it has at least one x-ray diffraction peak at a d spacing of about 3.9±0.15 Å and when M is either Mo or a mixture of W and Mo and M' is V and y>0 then the composition has a surface area of at least 25 $m^2/g$.

2. The composition of claim 1 where A is lithium.

3. The composition of claim 1 where M is molybdenum.

4. The composition of claim 1 where M is molybdenum, M' is vanadium and M" is antimony.

5. The composition of claim 1 further characterized in that the A cation has been exchanged for a secondary cation selected from the group consisting of hydronium ions, alkali ions, alkaline earth ions, lanthanide ions, divalent transition metal ions, trivalent transition metal ions, organic cations and mixtures thereof.

6. A crystalline metal oxide composition having an empirical formula of:

$$A_nNbM_xM'_yM''_mO_p$$

where A is a cation selected from the group consisting of an alkali metal ion, ammonium ion or mixtures thereof, M is molybdenum, tungsten and mixtures thereof, M' is tantalum and M" is selected from the group consisting of antimony, tellurium and mixture thereof, "n" varies from about 0.1 to about 2, "x" varies from about 0.01 to about 4, "y" varies from zero to about 4, "m" varies from zero to about 0.9 and "p" has a value such that it balances the valence of the combined elements, A Nb, M, M', M", the composition characterized in that it has at least one x-ray diffraction peak at a d spacing of about 3.9±0.15 Å.

7. The composition of claim 6 where A is lithium.

8. The composition of claim 6 where M is molybdenum.

9. The composition of claim 6 further characterized in that the A cation has been exchanged for a secondary cation selected from the group consisting of hydronium ions, alkali ions, alkaline earth ions, lanthanide ions, divalent transition metal ions, trivalent transition metal ions, organic cations and mixtures thereof.

10. A process for preparing a crystalline metal oxide composition having an empirical formula of:

$$A_nNbM_xM'_yM''_mO_p$$

where A is a cation selected from the group consisting of an alkali metal ion, an ammonium ion or mixtures thereof, M is molybdenum, tungsten or mixtures thereof, M' is selected from the group consisting of vanadium, tantalum and mixtures thereof, and M" is selected from the group consisting of antimony, tellurium and mixtures thereof, "n" varies from about 0.1 to about 2, "x" varies from about 0.01 to about 4, "y" varies from zero to about 4, "m" varies from zero to about 0.9 and "p" has a value such that it balances the valence of the combined elements, A, Nb, M, M', M", the composition characterized in that it has at least one x-ray diffraction peak at a d spacing of about 3.9±0, the process comprising forming a reaction mixture containing reactive sources of A, niobium, M, optionally M' and optionally M" at a temperature and a time sufficient to form the crystalline composition, the mixture having a composition expressed in terms of mole ratios of oxides of:

$$aA_2O:NbO_{5/2}:bMO_3:cM'O_{5/2}:dM''O_{q/2}:eH_2O$$

where "a" has a value from about 0.75 to about 4, "b" has a value of about 0.02 to about 5, "c" has a value from 0 to about 5, "d" has a value from 0 to about 1, "q" is the valence of M", and "e" has a value of about 10 to about 500.

11. The process of claim 10 where the temperature varies from about 100° C. to about 225° C. and the time varies from about 1 hour to about 96 hours.

12. The process of claim 10 where the alkaline metal source is selected from the group consisting of halide, acetate, hydroxide and carbonate compounds of the alkali metals.

13. The process of claim 10 where the niobium source is selected from the group consisting of niobium oxide, hydrous niobium oxide, niobium ethoxide, and ammonium niobium oxalate.

14. The process of claim 10 where the vanadium source is selected from the group consisting of vanadium (V) oxide, vanadium (V) oxychloride, vanadium oxide sulfate, and ammonium vanadate.

15. The process of claim 10 where the molybdenum source is selected from the group consisting of molybdic acid $((NH_4)_6Mo_7O_{24}.4H_2O)$, molybdenum trioxide $(MoO_3)$, sodium molybdate, and molybdenum (VI) oxychloride.

16. The process of claim 10 where the W source is selected from the group consisting of ammonium tungstate, tungsten (VI) oxide, tungsten (VI) chloride, sodium tungstate, and tungstic acid.

17. The process of claim 10 further characterized in that the A cation is exchanged for a secondary cation selected from the group consisting of hydronium ions, alkali ions, alkaline earth ions, lanthanide ions, divalent transition metal ions, trivalent transition metal ions, organic cations and mixtures thereof by contacting the composition with solution containing at least one of said secondary cation at exchange conditions thereby exchanging the A cation for the secondary cation.

18. The product of the process of claim 10.

19. The product of the process of claim 17.

20. A process for the ammoxidation of alkanes comprising reacting an alkane with ammonia in the presence of oxygen over an ammoxidation catalyst at ammoxidation conditions to produce a nitrile, where the alkane is selected from the group consisting of propane, isobutane and mixtures thereof and the ammoxidation catalyst comprises a crystalline composition having an empirical formula of:

$$A_nNbM_xM'_yM''_mO_p$$

where A is a cation selected from the group consisting of an alkali metal ion, ammonium ion or mixtures thereof, M is molybdenum, tungsten or mixtures thereof, M' is selected from the group consisting of vanadium, tantalum and mixtures thereof, and M" is selected from the group consisting of antimony, tellurium and mixtures thereof, "n" varies from about 0.1 to about 2, "x" varies from about 0.01 to about 4, "y" varies from zero to about 4, "m" varies from zero to about 0.9 and "p" has a value such that it balances the valence of the combined elements, A, Nb, M, M', M", the composition characterized in that it has at least one x-ray diffraction peak at a d spacing of about 3.9±0.15 Å and when M is either Mo or a mixture of W and Mo and M' is V and y>0 then the composition has a surface area of at least 25 $m^2/g$.

21. The process of claim 20 where the alkane is propane.

22. The process of claim 20 where the alkane is isobutane.

23. The process of claim 20 where the source of oxygen is air.

24. The process of claim 20 where the ammoxidation conditions include a temperature of about 350° C. to about 700° C., an hourly space velocity of about 100 to about 10,000 $hr^{-1}$, an ammonia to alkane mole ratio of about 0.5:1 to about 3:1, an oxygen to ammonia mole ratio of about 0.5:1 to about 10:1.

\* \* \* \* \*